United States Patent
Masuda et al.

(10) Patent No.: US 11,816,873 B2
(45) Date of Patent: Nov. 14, 2023

(54) IMAGE ANALYSIS DEVICE, IMAGE ANALYSIS METHOD, AND PROGRAM

(71) Applicant: SHISEIDO COMPANY, LTD., Tokyo (JP)

(72) Inventors: Yuji Masuda, Tokyo (JP); Megumi Sekino, Tokyo (JP); Hironobu Yoshikawa, Tokyo (JP); David Christopher Berends, Princeton, NJ (US); Michael Anthony Isnardi, Princeton, NJ (US); Yuzheng Zhang, Princeton, NJ (US)

(73) Assignee: Shiseido Company, Ltd., Tokyo (JP)

( * ) Notice: Subject to any disclaimer, the term of this patent is extended or adjusted under 35 U.S.C. 154(b) by 425 days.

(21) Appl. No.: 17/273,960

(22) PCT Filed: Sep. 4, 2019

(86) PCT No.: PCT/JP2019/034708
§ 371 (c)(1),
(2) Date: Mar. 5, 2021

(87) PCT Pub. No.: WO2020/050296
PCT Pub. Date: Mar. 12, 2020

(65) Prior Publication Data
US 2021/0334575 A1     Oct. 28, 2021

Related U.S. Application Data

(60) Provisional application No. 62/727,994, filed on Sep. 6, 2018.

(51) Int. Cl.
*G06V 10/141*  (2022.01)
*G06T 7/90*    (2017.01)
*G06V 10/56*   (2022.01)

(52) U.S. Cl.
CPC .......... *G06V 10/141* (2022.01); *G06T 7/90* (2017.01); *G06V 10/56* (2022.01); *G06T 2207/30196* (2013.01)

(58) Field of Classification Search
None
See application file for complete search history.

(56) References Cited

U.S. PATENT DOCUMENTS 9,787,965 B2 * 10/2017  Tozuka ................. H04N 9/643
10,545,497 B1 *  1/2020  Cui ..................... G05D 1/0016
(Continued)

FOREIGN PATENT DOCUMENTS

JP    06-109441 A    4/1994
JP    2015-046142 A    3/2015
(Continued)

*Primary Examiner* — Delomia L Gilliard
(74) *Attorney, Agent, or Firm* — Foley & Lardner LLP

(57) ABSTRACT

An image analysis device according to the present invention includes: an image capturing unit that captures a subject; a light emitting unit that emits light to the subject; a sensor unit that senses an inclination of the image capturing unit relative to the subject; a control unit that causes the image capturing unit to capture an image of the subject while controlling light emission of the light emitting unit; and a determination unit that, based on a positional relationship of the image capturing unit and the light emitting unit and the inclination, determines a measurement region spaced apart by a predetermined distance from a reflection region corresponding to a position in the image where a light from the light emitting unit regularly reflects at the subject.

11 Claims, 16 Drawing Sheets

(56) References Cited

U.S. PATENT DOCUMENTS

| | | | |
|---|---|---|---|
| 2010/0007751 A1* | 1/2010 | Icho | H04N 23/80 348/222.1 |
| 2010/0103311 A1* | 4/2010 | Makii | H04N 5/2621 348/E5.04 |

FOREIGN PATENT DOCUMENTS

| | | |
|---|---|---|
| JP | 2018-034064 A | 3/2018 |
| JP | 2018-045464 A | 3/2018 |

* cited by examiner

[Fig.1]
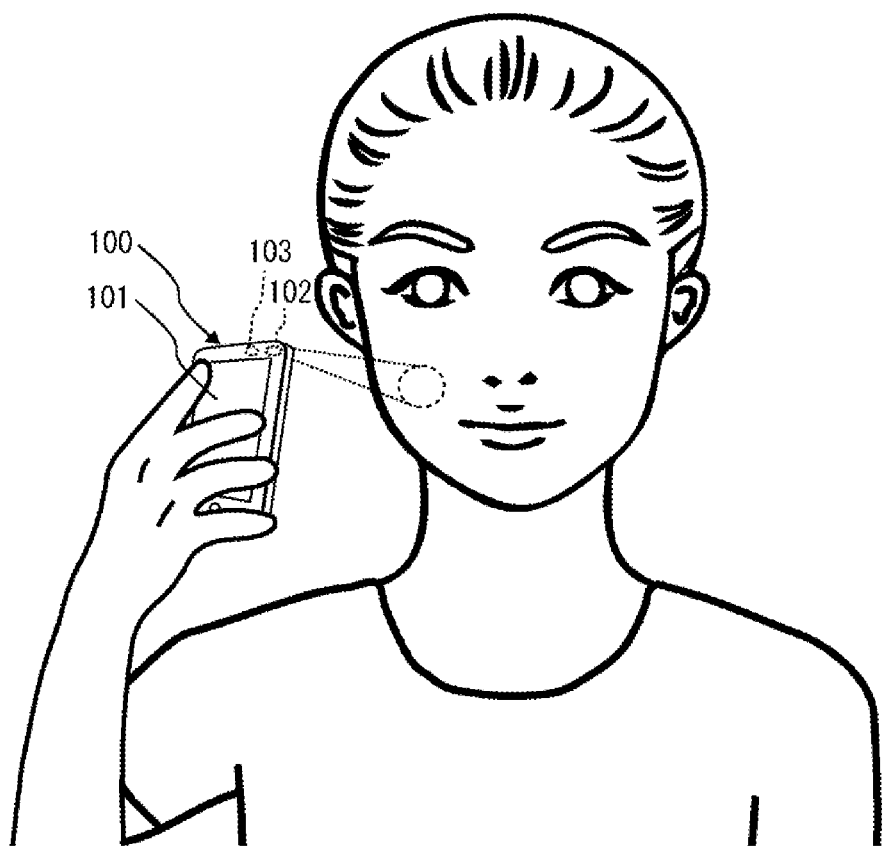

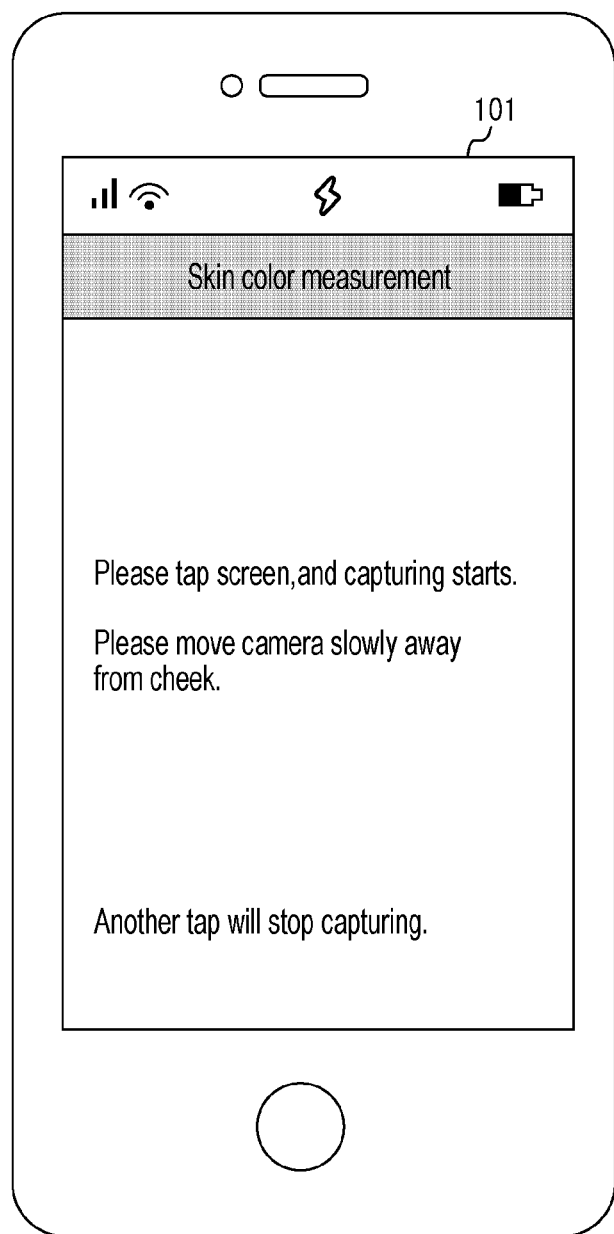

[Fig.3]
100
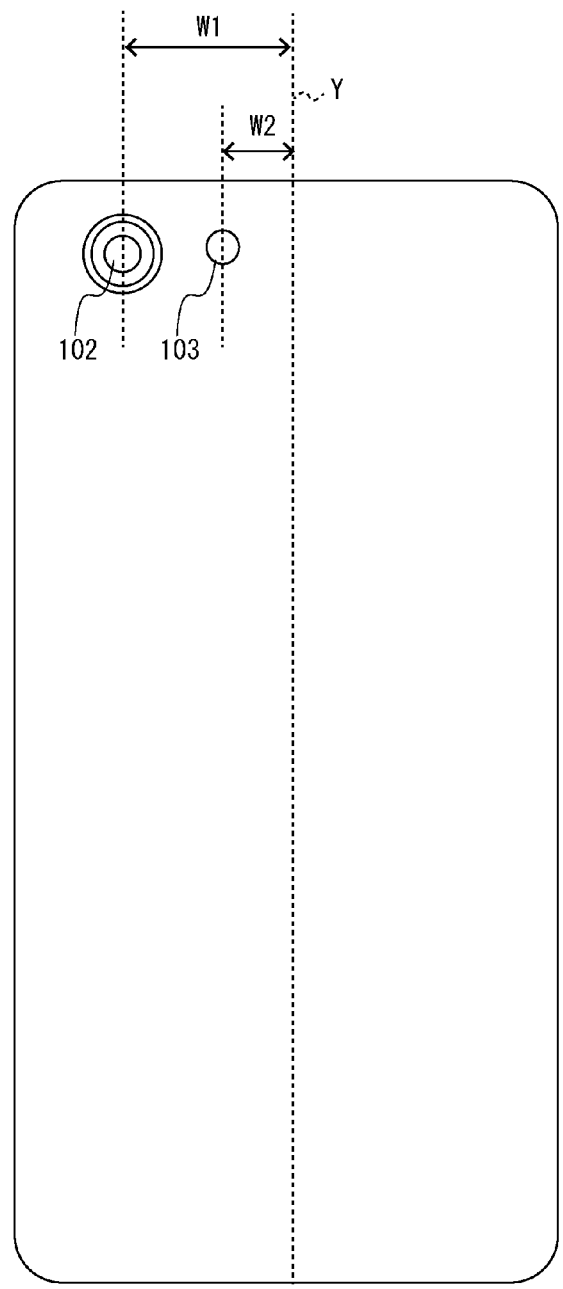

[Fig.4]
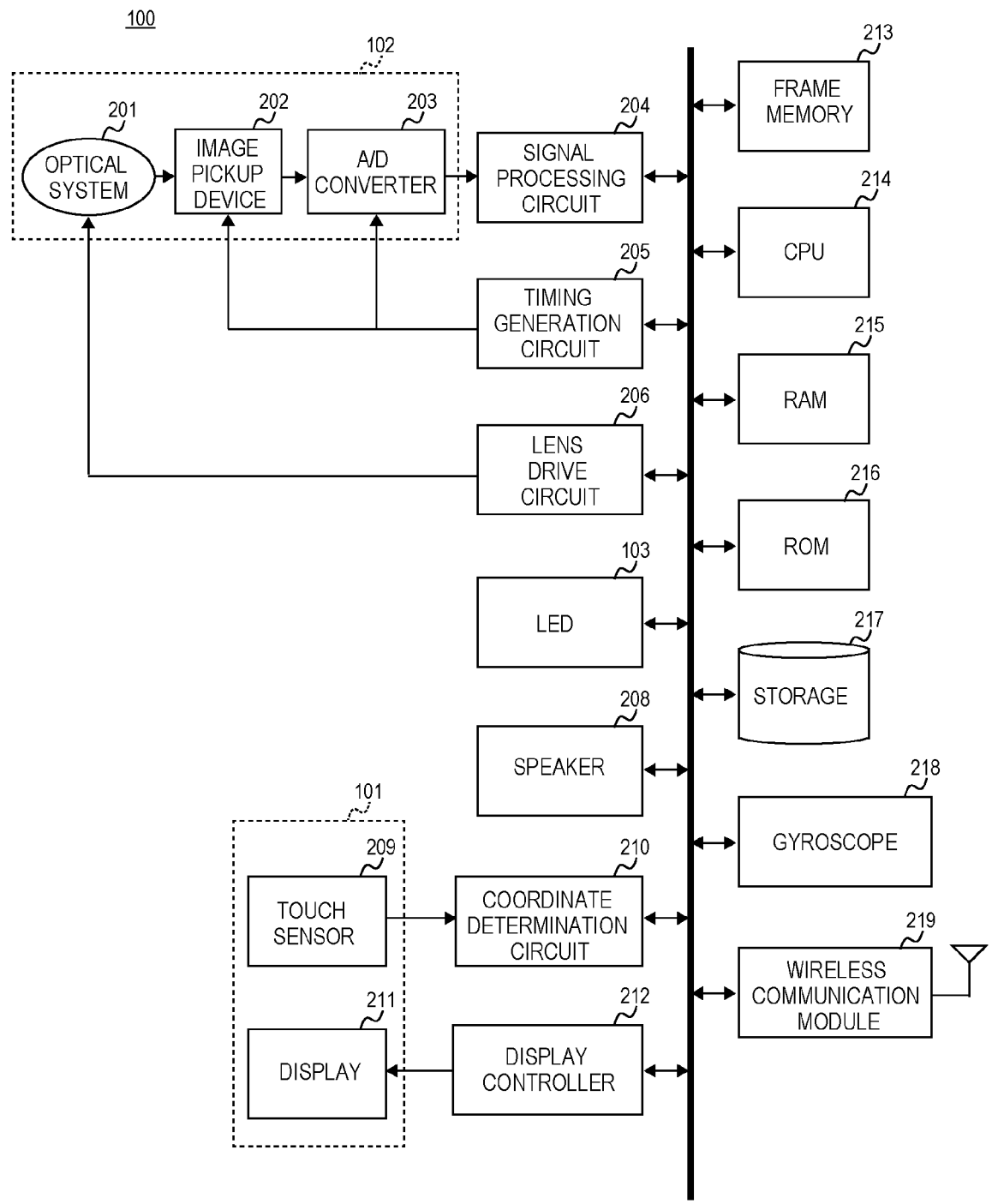

[Fig.5]
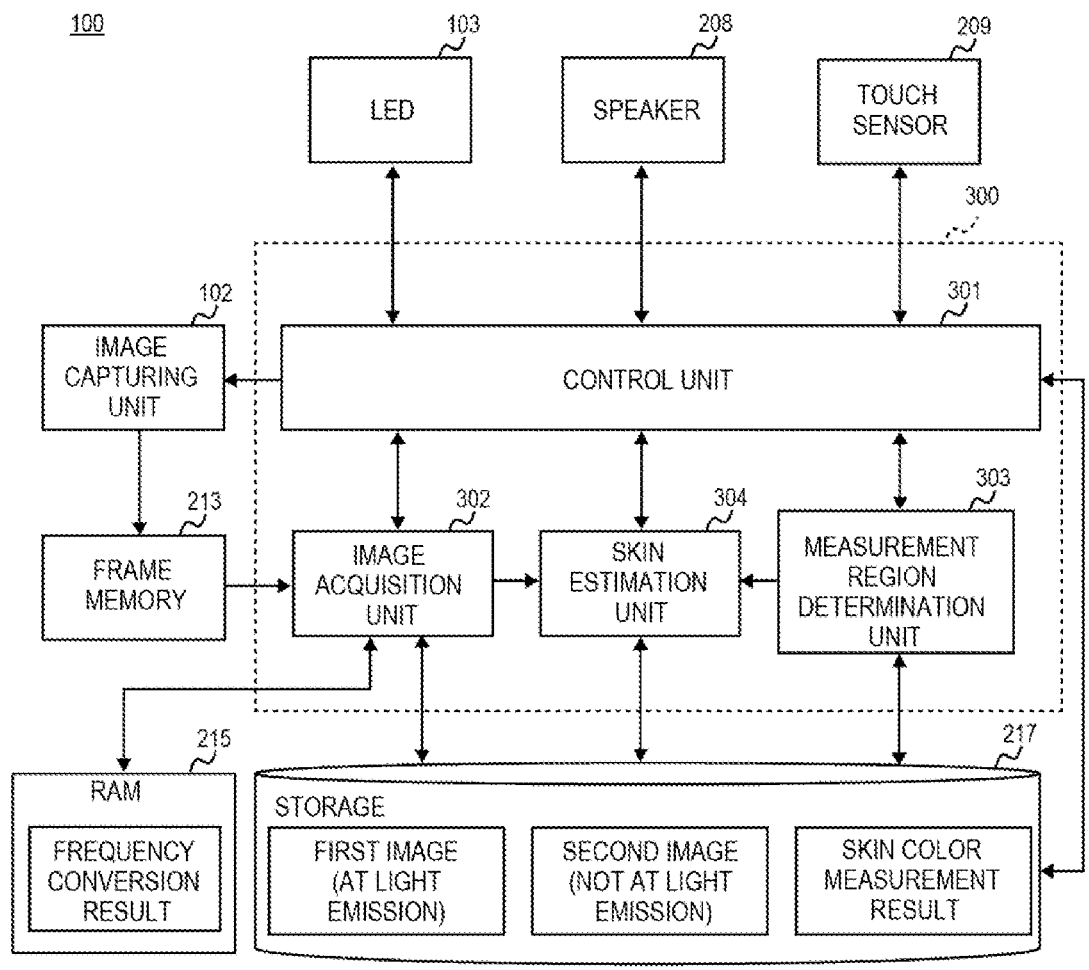

[Fig.6]
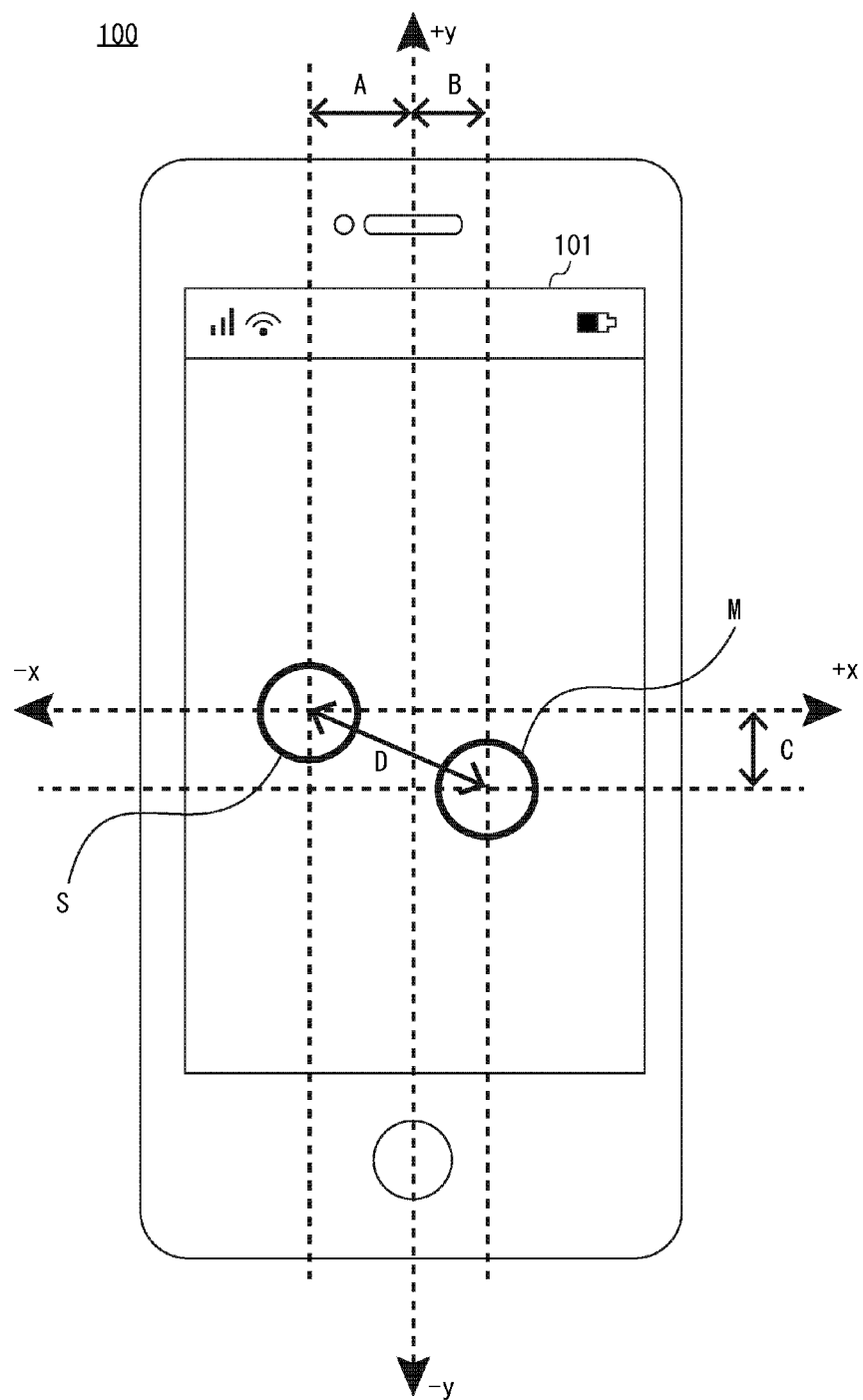

[Fig.7]
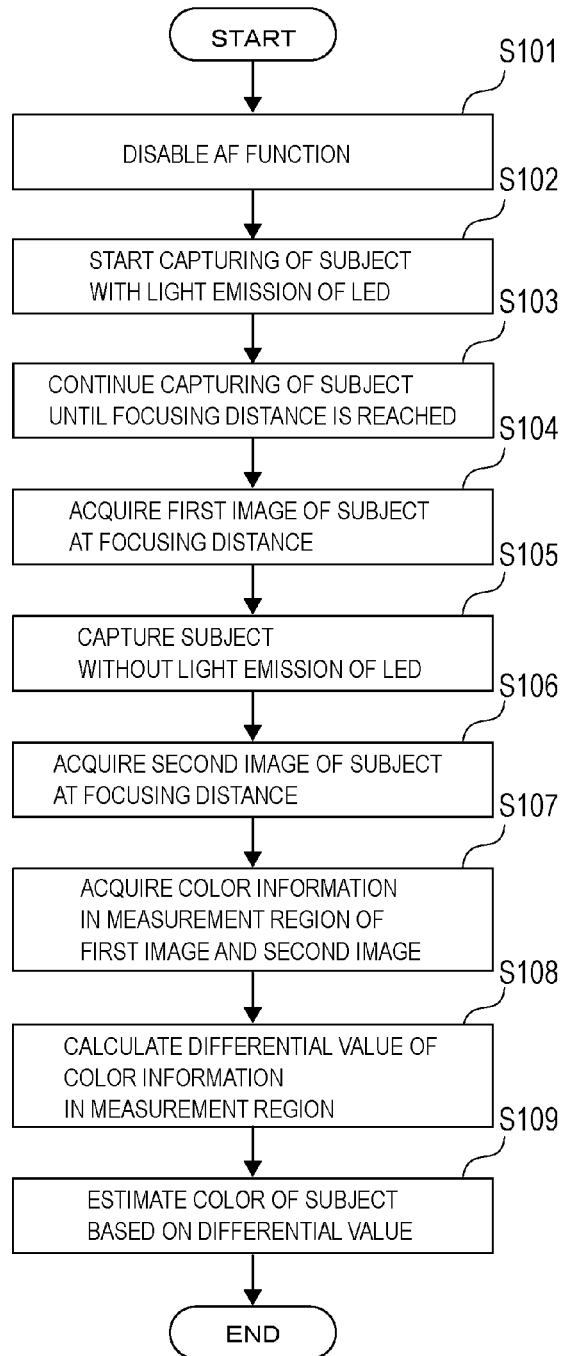

[Fig.8]
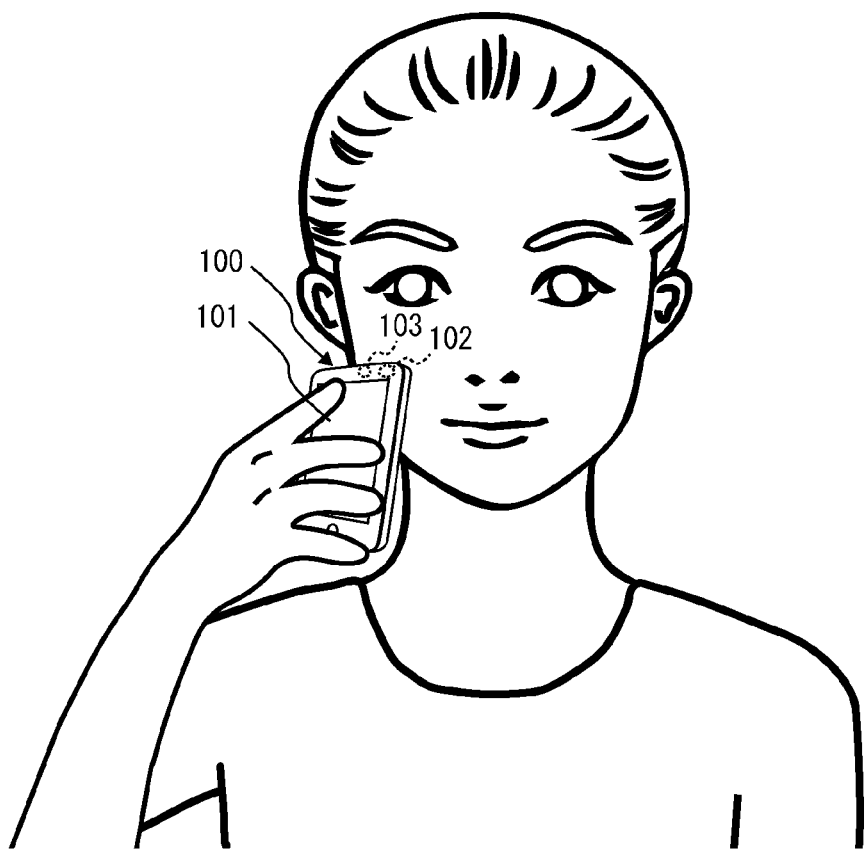

[Fig.9]
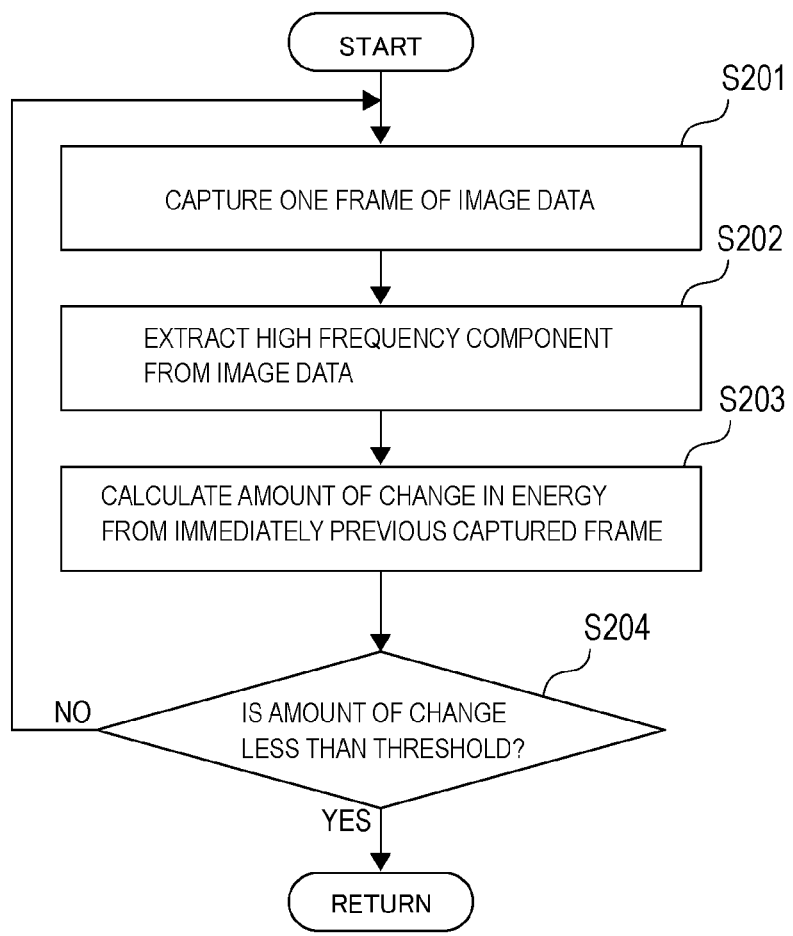

[Fig.10]
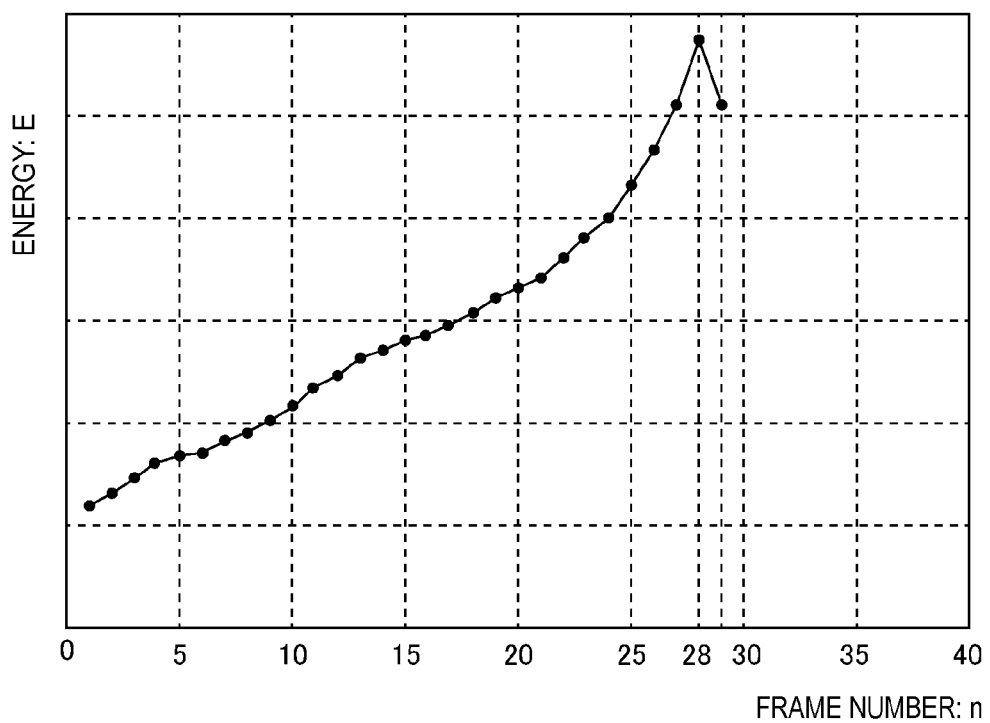

[Fig.11]
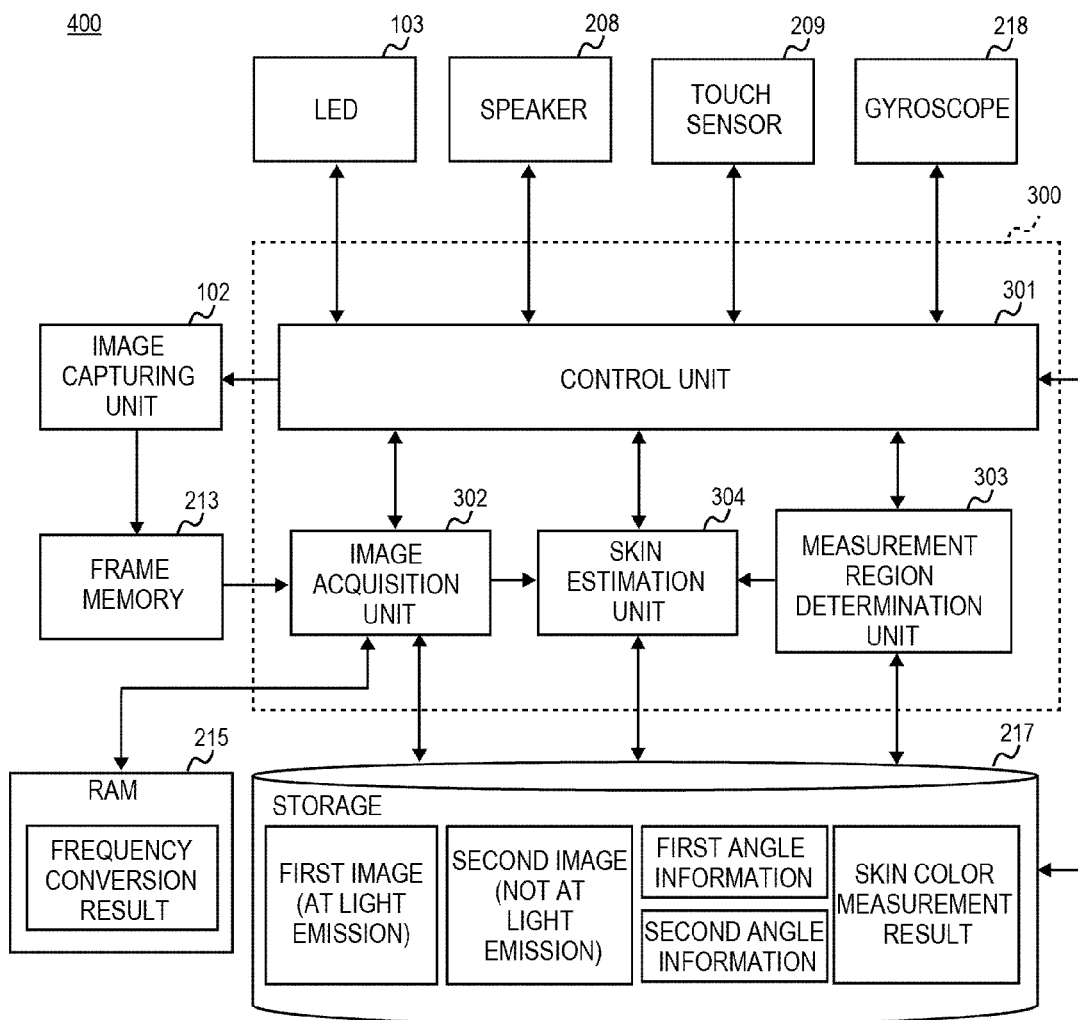

[Fig.12A]
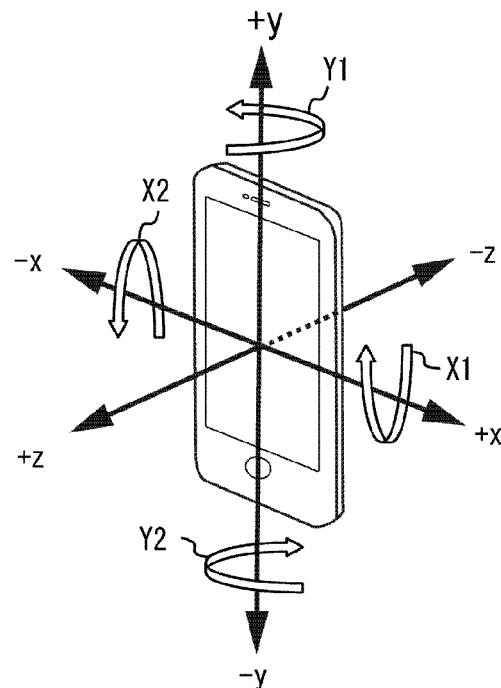
[Fig.12B]
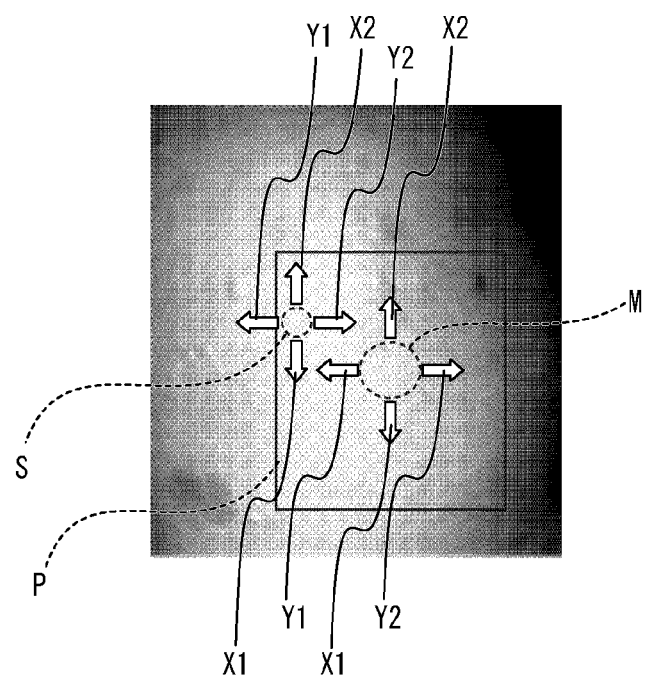

[Fig.13]
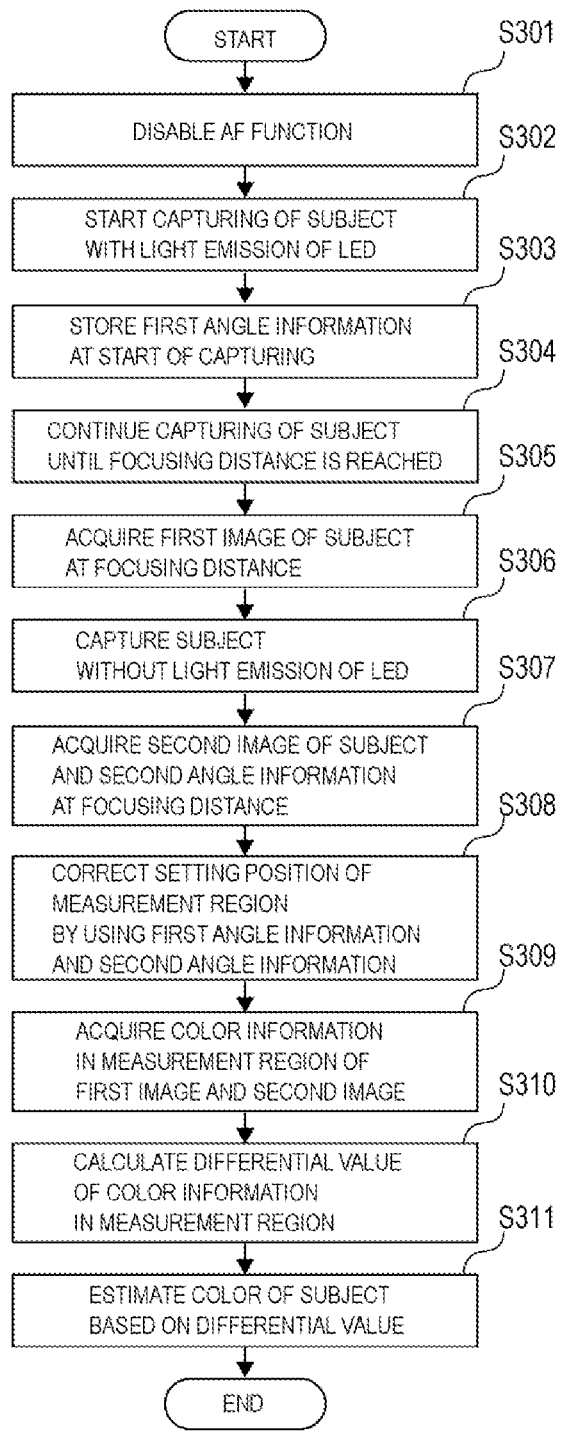

[Fig.14]
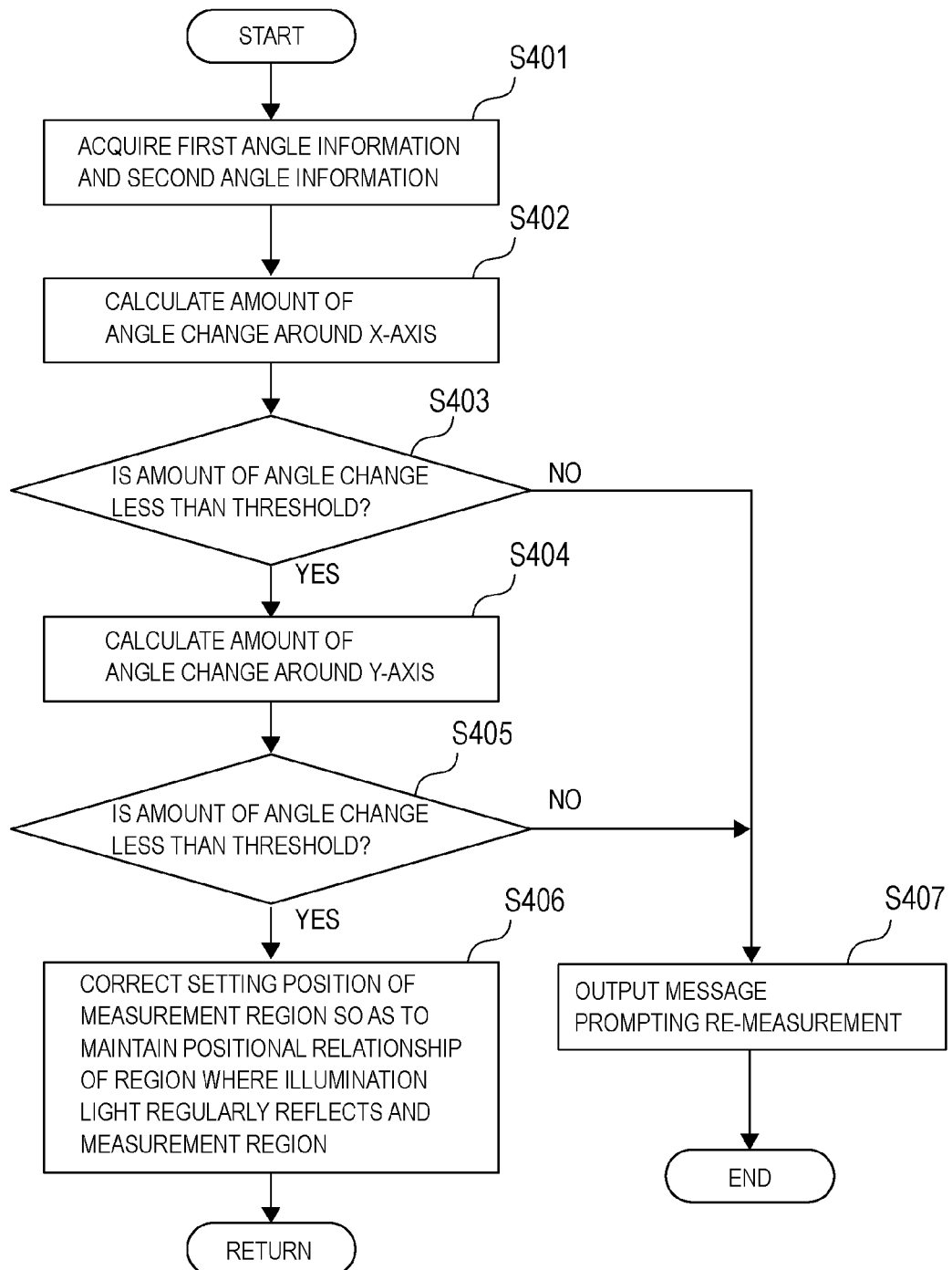

[Fig.15]
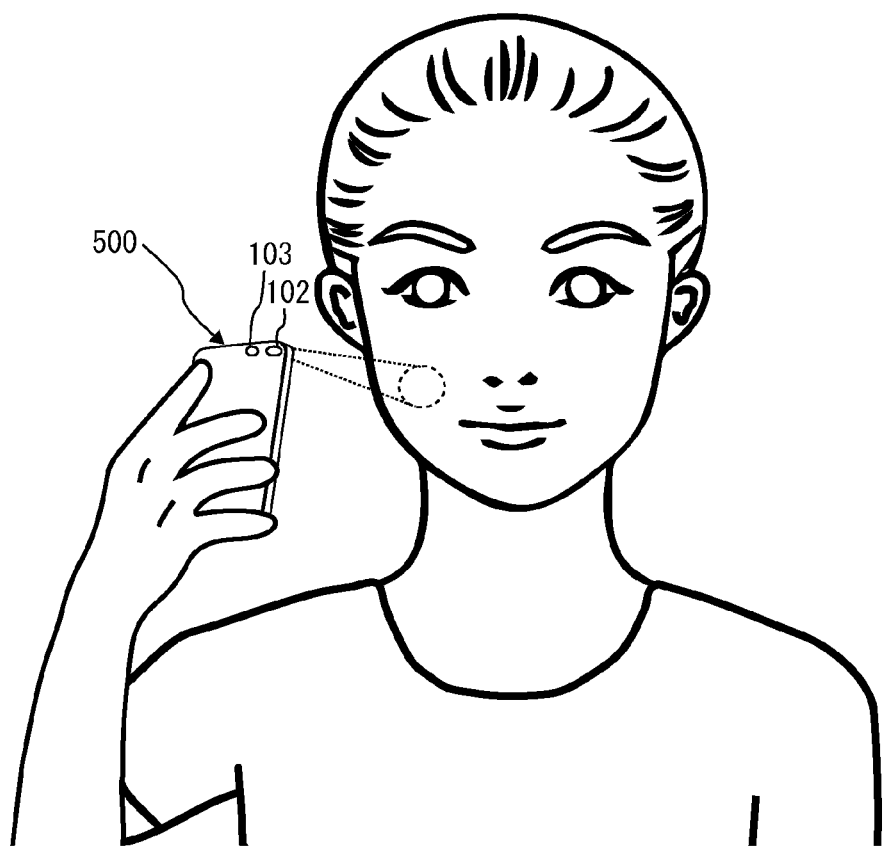

[Fig.16]
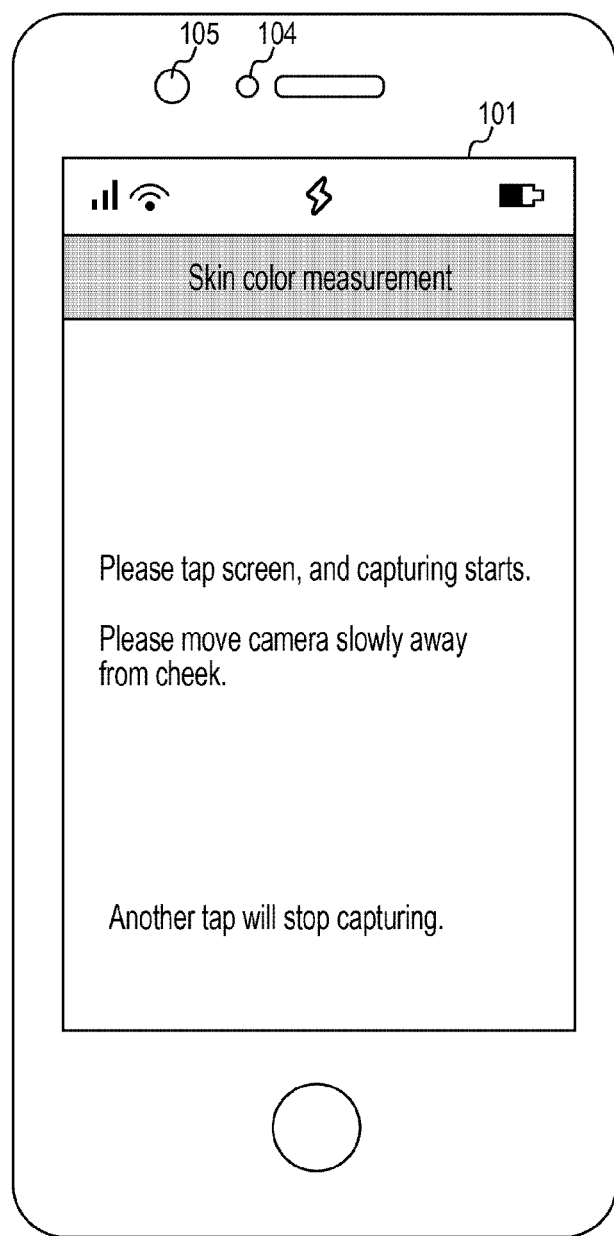

IMAGE ANALYSIS DEVICE, IMAGE ANALYSIS METHOD, AND PROGRAM

CROSS-REFERENCE TO RELATED APPLICATIONS

This application is the U.S. National Stage of PCT/JP2019/034708, filed Sep. 4, 2019, which claims priority to U.S. Provisional application No. 62/727,994, filed Sep. 6, 2018.

TECHNICAL FIELD

The present invention relates to an image analysis device, an image analysis method, and a program that analyze an image of a subject to measure the color of the subject.

BACKGROUND ART

In recent years, colorimeter devices that capture an image of a subject (for example, a person or an object) by using an image capturing device such as a digital camera and analyze the captured image to measure the color of the subject are known. For example, Patent Literature 1 discloses a colorimeter device that captures images of color samples (standard color chart) and a subject, respectively, to acquire RGB data and corrects the RGB data of the subject based on the RGB data of the color samples and color standard values of the color samples.

Further, Patent Literature 2 discloses a color converter device that creates in advance a plurality of color profiles representing a relationship between a standard colorimetric value in accordance with a plurality of illumination conditions and RGB data of an image captured by a digital camera and measures the color of a subject based on RGB data acquired by image capturing of the subject, an illumination condition at the image capturing, and the corresponding color profile.

CITATION LIST

Patent Literature

PTL 1: Japanese Patent Application Laid-Open No. 2018-34064
PTL 2: Japanese Patent Application Laid-Open No. 2015-46142

SUMMARY OF INVENTION

Technical Problem

The colorimeter device disclosed in Patent Literature 1 uses not only color samples but also a light-shielding member for preventing a subject from being irradiated with an external light other than a light from a light source when measuring the color of the subject. It is therefore difficult for the user to use the colorimeter device to measure the color at home or the like.

Further, while the colorimeter device disclosed in Patent Literature 2 does not require color samples when measuring the color of a subject, it is necessary to prepare in advance color profiles corresponding to a plurality of illumination conditions and select the optimal color profile. When a subject is continuously captured with a constant illumination condition, however, a change in the inclination (angle) of the device relative to the subject causes a measurement region to move to a different position resulting in a reduction in accuracy of measurement.

Accordingly, in view of the above problem, the present invention intends to provide an image analysis device, an image analysis method, and a program that can easily and accurately measure the color of a subject even when the attitude of the device relative to the subject is changed during image capturing.

Solution to Problem

According to one aspect of the present invention, provided is an image analysis device including: an image capturing unit that captures a subject; a light emitting unit that emits light to the subject; a sensor unit that senses an inclination of the image capturing unit relative to the subject; a control unit that causes the image capturing unit to capture an image of the subject while controlling light emission of the light emitting unit; and a determination unit that, based on a positional relationship of the image capturing unit and the light emitting unit and the inclination, determines a measurement region spaced apart by a predetermined distance from a reflection region corresponding to a position in the image where a light from the light emitting unit regularly reflects at the subject.

According to another aspect of the present invention, provided is an image analysis method including steps of: causing an image capturing device to capture an image of a subject while controlling light emission of a light emitting device to the subject; sensing an inclination of the image capturing device relative to the subject by using a sensor; and based on a positional relationship of the image capturing device and the light emitting device and the inclination, determining a measurement region spaced apart by a predetermined distance from a reflection region corresponding to a position in the image where a light from the light emitting device regularly reflects at the subject.

According to yet another aspect of the present invention, provided is a program that causes a computer to perform steps of: causing an image capturing device to capture an image of a subject while controlling light emission of a light emitting device to the subject; sensing an inclination of the image capturing device relative to the subject by using a sensor; and based on a positional relationship of the image capturing device and the light emitting device and the inclination, determining a measurement region spaced apart by a predetermined distance from a reflection region corresponding to a position in the image where a light from the light emitting device regularly reflects at the subject.

Advantageous Effects of Invention

According to the present invention, the color of a subject can be easily and accurately measured even when the attitude of the device relative to the subject is changed during image capturing.

BRIEF DESCRIPTION OF DRAWINGS

FIG. 1 is a diagram illustrating a state during measurement of an image analysis device according to a first embodiment.
FIG. 2 is a front view of the image analysis device according to the first embodiment.
FIG. 3 is a backside view of the image analysis device according to the first embodiment.

FIG. 4 is a block diagram illustrating an example of a hardware configuration of the image analysis device according to the first embodiment.

FIG. 5 is a functional block diagram of the image analysis device according to the first embodiment.

FIG. 6 is a diagram illustrating a positional relationship between a reflection region and a measurement region of an illumination light from a light emitting unit in a subject according to the first embodiment.

FIG. 7 is a flowchart illustrating an example of a process performed in the image analysis device according to the first embodiment.

FIG. 8 is a diagram illustrating a state at the start of measurement in the image analysis device according to the first embodiment.

FIG. 9 is a flowchart illustrating details of an image capturing process according to the first embodiment.

FIG. 10 is a graph illustrating a change in energy of a high frequency component according to the first embodiment.

FIG. 11 is a functional block diagram of an image analysis device according to a second embodiment.

FIG. 12A and FIG. 12B are diagrams illustrating correction of a measurement region in accordance with an attitude state of the image analysis device according to the second embodiment.

FIG. 13 is a flowchart illustrating an example of a process performed in the image analysis device according to the second embodiment.

FIG. 14 is a flowchart illustrating an example of a correction process of a measurement region according to the second embodiment.

FIG. 15 is diagram illustrating a state during measurement in an image analysis device according to a modified embodiment.

FIG. 16 is a front view illustrating an example of an operating window displayed on the image analysis device according to the modified embodiment.

DESCRIPTION OF EMBODIMENTS

First Embodiment

FIG. 1 is a diagram illustrating a state during measurement in an image analysis device 100 according to the present embodiment. FIG. 2 is a front view of the image analysis apparatus 100, and FIG. 3 is a backside view of the image analysis device 100. The image analysis device 100 may be a portable information terminal such as a smartphone, a tablet computer, or the like, for example. A case of a smartphone will be described below as an example of the image analysis device 100.

The image analysis device 100 is provided with a touchscreen (display) 101 on the front side. Further, the image analysis device 100 is provided with an image capturing unit 102 in the upper part on the backside and a light emitting diode (LED) 103 that is a light emitting unit. In this way, in the present embodiment, the image capturing unit 102 and the LED 103 are provided on the surface opposite to the touchscreen 101 that displays an operating window, respectively. The image capturing unit 102 is provided at a position of a distance W1 from a center axis (Y-axis) of the image analysis device 100, and the LED 103 is provided at a position of a distance W2 (W2<W1) from the center axis (see FIG. 3).

Further, an application program used for measuring the color of a subject (hereafter, referred to as "measuring application") is installed in advance within the image analysis device 100. The measuring application may be downloaded from a network (not illustrated) or may be supplied to the image analysis device 100 via a storage medium such as a memory card or a personal computer. Note that a subject in the present embodiment is a cheek of a user, and it is assumed that the image analysis device 100 measures a skin color of a cheek (see FIG. 1).

An icon of the measuring application is displayed on the touchscreen 101 (not illustrated), and the measuring application starts up in response to the user touching the icon (see FIG. 2). When the user holds and moves the image analysis device 100 closer to or away from a subject (cheek) while directing the image capturing unit 102 to the subject, the image analysis device 100 automatically captures a focused image. The image analysis device 100 can analyze the captured image and display the analysis result on the touchscreen 101.

FIG. 4 is a block diagram illustrating an example hardware configuration of the image analysis device 100 according to the present embodiment. The image analysis device 100 has the image capturing unit 102, the LED 103, a signal processing circuit 204, a timing generation circuit 205, a lens drive circuit 206, a speaker 208, a touch sensor 209, and a coordinate determination circuit 210. Furthermore, the image analysis device 100 has a display 211, a display controller 212, a frame memory 213, a central processing unit (CPU) 214, a random access memory (RAM) 215, a read only memory (ROM) 216, storage 217, a gyroscope 218, and a wireless communication module 219. These devices are connected to each other via buses.

The image capturing unit 102 has an optical system 201, an image pickup device 202, and an analog-to-digital (A/D) converter 203. The optical system 201 includes an optical filter, a fixed lens, and a focus lens and captures a light from a subject (captured part) onto an image capturing plane of the image pickup device 202 to form a subject image. The image pickup device 202 may be a Complementary Metal Oxide Semiconductor (CMOS) image sensor or a Charge Coupled Device (CCD) image sensor, for example, and has multiple pixels, color filters, and micro lenses that are two-dimensionally arranged. The multiple pixels may include pixels used for image capturing and pixels used for focus detection. Further, the image pickup device 202 has an electronic shutter function that controls charge accumulation time. The multiple pixels output pixel signals based on an incident light from the optical system 201, respectively.

The A/D converter 203 is formed of a comparator circuit, a latch circuit, or the like and converts an analog pixel signal from the image pickup device 202 into digital image data. The A/D converter 203 may be provided within the image pickup device 202. The image capturing unit 102 can output not only a static image but also a moving image of a predetermined framerate. The framerate may be any value such as ¼ seconds, 1/30 seconds, 1/60 seconds, or the like, for example.

The signal processing circuit 204 includes a numeric value calculation circuit and performs digital signal processing such as white balance adjustment, gamma correction, pixel interpolation, contour emphasis, gradation conversion, noise reduction, compression, or the like on image data from the A/D converter 203. The lens drive circuit 206 has an actuator or the like, which drives a focus lens of the optical system 201 to adjust a focus distance. The timing generation circuit 205 outputs a timing signal such as a clock signal, a synchronization signal, or the like to the image pickup device 202 and the A/D converter 203.

The LED 103 is a light source provided near the optical system 201. The LED 103 is used as a lighting unit that irradiates a captured part with a light for obtaining illuminance suitable for image capturing. The LED 103 may be formed of a plurality of LEDs 103 having different light colors and can emit a light with a color temperature and chroma suitable for a captured part by adjusting the intensity of light emission of each of the LEDs 103. The speaker 208 has a piezoelectric vibration unit and is driven by a current drive circuit. The speaker 208 outputs an audio signal such as a music, a message, sound effects, or the like and is used as a notification unit that notifies the user of completion of image capturing.

The touch sensor 209 is a capacitive sensor having transparent electrodes arranged in a matrix and is provided on the display 211. In response to the finger of the user touching the touch sensor 209, the electrostatic capacitance on the electrode changes. The coordinate determination circuit 210 can detect a change in the electrostatic capacitance on the touch sensor 209 and calculate the position touched by the finger of the user. The touch sensor 209 is used as an operating unit that accepts an instruction from the user.

The display 211 is a Thin Film Transistor (TFT) liquid crystal display or an organic Electro Luminescence (EL) display, for example, and displays an image, a moving image, a text, an icon, or the like in accordance with a display signal from the display controller 212. The display controller 212 is a processor including video memory and controls the display on the display 211. The display controller 212 temporarily stores display data from the CPU 214 and generates and outputs a display signal to the display 211. The touch sensor 20 and the display 211 are integrally formed to configure the touchscreen 101.

The frame memory 213 can temporarily hold multiple frames of image data and may be used in image processing in the signal processing circuit 204 and the CPU 214. For example, the signal processing circuit 204 may perform image stabilizing or noise reduction by detecting a motion vector in multiple frames of image data. Further, in moving-image capturing, the frame memory 213 can store temporally continuous multiple frames of image data therein. Note that a part of the RAM 215 may be used as the frame memory 213. The CPU 214 has a CPU core, cache memory, or the like and integrally controls respective devices of the image analysis device 100. The CPU 214 reads and executes a predetermined program from the ROM 216 or the storage 217 to implement respective functions of the image analysis device 100.

The RAM 215 is a Dynamic RAM (DRAM), for example, and is used for a work field of the CPU 214, a load field of a program, or the like. The ROM 216 is an Electrically Erasable Programmable ROM (EEPROM), for example, and stores Basic Input Output System (BIOS), various setting files, or the like. The storage 217 is a flash memory, for example, and stores a basic program such as Operating System (OS) or various application programs such as the measuring application. The storage 217 also stores various data such as a measurement result obtained by the measuring application, an image or a moving image captured by the image capturing unit 102.

The gyroscope 218 is formed of a piezoelectric oscillation element and senses the orientation of the image analysis device 100. The image analysis device 100 may further have a Global Positioning System (GPS) sensor, an illuminance sensor, a proximity sensor, an acceleration sensor, or the like.

The wireless communication module 219 is an interface used for wireless communication with a communication network such as the Internet. The wireless communication module 219 includes an antenna (not illustrated) and connects itself to the communication network by using a mobile communication scheme such as Long Term Evolution (LTE), 4th Generation (4G), or the like or a wireless communication scheme such as a wireless Local Area Network (LAN). The wireless communication module 219 can transmit and receive data to and from an external device via the communication network.

FIG. 5 is a functional block diagram of the image analysis device 100 according to the present embodiment. The image analysis device 100 has a control unit 301, an image acquisition unit 302, a measurement region determination unit 303, and a skin color estimation unit 304. The function of each unit is implemented by the CPU 214 reading a measuring application 300 stored in the ROM 216 or otherwise the storage 217 to the RAM 215 and executing the measuring application 300.

The control unit 301 controls the operation of the image capturing unit 102, the LED 103, and the speaker 208. The control unit 301 has an autofocus (AF) function and can adjust the focus distance of the image capturing unit 102. In an AF process, the control unit 301 controls the position of the focus lens of the optical system 201 through the lens drive circuit 206 so that the contrast of the captured image becomes the maximum. The control unit 301 may perform an AF process with an image capturing plane phase difference scheme without being limited to the AF process by using the contrast scheme. However, the control unit 301 of the present embodiment disables the autofocus function when performing the measuring application 300.

Further, the control unit 301 has an auto-exposure (AE) function and can control the ISO sensitivity of the image pickup device 202 and the speed of the electronic shutter. The control unit 301 can set the AF function or the AE function to be enabled or disabled. Furthermore, the control unit 301 controls the LED 103 and the speaker 208 and acquires an instruction from the user via the touch sensor 209.

Further, the control unit 301 acquires image data in which a subject is captured with light emission of the LED 103 (hereafter, referred to as "first image") and an image data in which the same subject as in the first image is captured without light emission of the LED 103 (hereafter, referred to as "second image") via an image acquisition unit 302 described later. The control unit 301 causes the image capturing unit 102 to continuously capture the first image and the second image while performing switch control of the light emission of the LED 103 when a subject is located at a focusing distance of the image capturing unit 102. A light entering the image pickup device 202 when the first image is captured includes two lights of an external light and an illumination light from the LED 103. On the other hand, a light entering the image pickup device 202 when the second image is captured is only the external light.

The image acquisition unit 302 reads multiple frames of image data captured with the LED 103 emitting light (first image) from the frame memory 213 and acquires the sharpest image data out of the multiple frames of image data. The image acquisition unit 302 can extract a frequency component based on the sharpness of the captured part from the image data and determine focusing of image data based on the frequency component. The image acquisition unit 302 then stores, in the storage 217, image data for the first image captured at the focusing distance.

The image acquisition unit 302 extracts a frequency component using a frequency conversion such as Fourier transformation. Data such as the frequency spectral obtained as a result of frequency conversion is held in the RAM 215. The frequency conversion may be wavelet transformation, Laplacian operation, discrete cosine transformation, Hadamard transformation, Karhunen-Loeve (KL) transformation, or the like without being limited to Fourier transformation.

Further, when acquiring, from the frame memory 213, image data on the second image captured at a focusing distance without light emission of the LED 103, the image acquisition unit 302 stores the image data on the second image in the storage 217 in the same manner as the case of the first image.

The measurement region determination unit 303 determines a measurement region spaced apart by a predetermined distance from a reflection region corresponding to a position where a light from the LED 103 regularly reflects (mirror-reflects) at a subject in the first image and the second image based on a positional relationship between the image capturing unit 102 and the LED 103 illustrated in FIG. 3. That is, the measurement region is offset from the reflection region of the illumination light from the LED 103.

The skin color estimation unit 304 estimates a color of a subject in accordance with a differential value between color information of the first image and color information of the second image. Specifically, the skin color estimation unit 304 calculates a differential value for color information of a reference pixel included in a predetermined measurement region out of a pixel group forming the first image and the second image. The skin color estimation unit 304 then estimates the color of a subject in accordance with a predetermined algorithm that associates the calculated differential value, a known lighting condition, and a value in a color specification system of the measurement region. Note that the first image and the second image of the present embodiment include color information of an RGB color specification system, and the skin color estimation unit 304 estimates the color based on color information of an XYZ color specification system converted from the RGB color specification system.

FIG. 6 is a diagram illustrating a positional relationship of an illumination light of the LED 103 between a reflection region S and a measurement region M on a subject. In this example, when an image of a subject is displayed on the touchscreen 101, the reflection region S is spaced apart by a distance A in the left direction from the Y-axis of the image analysis device 100 and set at a position on the X-axis. Further, the measurement region M is set at a distance B in the right direction from the Y-axis of the image analysis device 100 and at a distance C downward from the X-axis thereof. Further, the inter-centroid distance of the reflection region S and the measurement region M is set to a distance D. In such a way, since the measurement region M is set at a position at a predetermined distance in a predetermined direction from the reflection region S, the image analysis device 100 can accurately measure the color of a subject without being excessively affected by an illumination light.

For example, when the reflection region S of the illumination light of the LED 103 with respect to a subject is located at 3.9 degrees relative to the Y-axis at focusing and when the angle between the measurement region M and the reflection region S is less than or equal to 7 degrees, the reflected light overlaps with the measurement region M. Further, when the angle between the measurement region M and the reflection region S is greater than or equal to 11 degrees, the illumination in the measurement region M becomes excessively dark. It is therefore preferable that the measurement region M be set at a position shifted from the position of the reflection region S by 7.5 degrees relative to the Y-axis (corresponding to the total distance of the distance A and the distance B on the screen of FIG. 6) and 3.5 degrees relative to the X-axis (corresponding to the distance C on the screen of FIG. 6). In this case, the inter-centroid distance D of the reflection region S and the measurement region M is set to 8.3 degrees when converted into angle information.

FIG. 7 is a flowchart illustrating an example of a process performed by the image analysis device 100 according to the present embodiment. An example in which the user measures the color (skin color) of a subject (cheek) using the measuring application 300 will be described here.

In the image analysis device 100, once the user starts up the measuring application 300, the control unit 301 disables the AF function of the image capturing unit 102 (step S101). That is, the control unit 301 sets the optical system 201 in a state of a fixed focus. The focusing distance may be defined here so that the size of the captured image becomes optimal in image analysis. For example, the focusing distance may range from 50 mm to 100 mm, or may be the shortest distance that can be set in the image capturing unit 102. The control unit 301 sets a light amount, a color temperature, a chroma of the LED 103 by which a lighting environment suitable for image capturing can be obtained and turns on the LED 103.

Next, in an initial state where the image analysis device 100 is in contact with the cheek of the user, for example, the control unit 301 starts capturing a subject by using the image capturing unit 102 while causing the LED 103 to emit light (step S102). Note that the control unit 301 preferably causes the image capturing unit 102 to capture the first image while also disabling the white balance function.

FIG. 8 is a diagram illustrating a state of the image analysis device 100 at the time of starting measurement. FIG. 8 illustrates here a case where the user taps the screen while causing the image analysis device 100 to be in contact with the cheek. Once the user starts up the measuring application 300 in such a way, the control unit 301 displays a message such as "Please tap screen, and capturing starts. Please move camera slowly away from cheek", for example, on the display 211 (see FIG. 2).

The control unit 301 may display an animation together with a message or may generate a message by voice. When the user moves the image capturing unit 102 closer to the subject (cheek) according to the message and taps the touchscreen 101 (see FIG. 1), the control unit 301 starts image capturing by using the image capturing unit 102. The image capturing is performed at a predetermined framerate (for example, 4 to 5 frames per second). Since the distance between the image capturing unit 102 and the captured part at the time of starting image capturing is shorter than the focusing distance, an initially captured image has a low sharpness.

Next, the control unit 301 continues the image capturing by using the image capturing unit 102 until the focusing distance from the subject (cheek) is reached (step S103). After tapping the touchscreen 101, the user moves the image capturing unit 102 gradually in the vertical direction away from the subject (cheek). Based on change in the sharpness of the image, the control unit 301 determines whether or not the image capturing unit 102 has moved to the focusing distance from the subject (cheek). Details of the image capturing process (step S103) will be described later.

Next, the image acquisition unit 302 acquires the captured image (first image) of a subject in a focusing distance (step S104). Specifically, the image acquisition unit 302 acquires image data having the largest energy of a high frequency component as the first image out of multiple frames of image data obtained by image capturing. The acquisition process of image data (step S104) may be performed at the same time as the image capturing process (step S103) described above.

Next, the control unit 301 captures a subject by using the image capturing unit 102 while stopping light emission of the LED 103 (step S105). In response, the image acquisition unit 302 acquires, from the frame memory 213, the captured image (second image) of the subject in a state without light emission and at the focusing distance (step S106). Note that the control unit 301 preferably causes the image capturing unit 102 to capture the second image while also disabling the white balance function.

Next, the skin color estimation unit 304 acquires color information in the measurement region of the first image and the second image (step S107). As described above, the measurement region is spaced apart by a predetermined distance away from the reflection region corresponding to the position where the light of the LED 103 regularly reflects (mirror-reflects) at the subject among the first image and the second image.

Next, the skin color estimation unit 304 calculates a differential value of color information in the common measurement region between the first image and the second image (step S108). Then, the skin color estimation unit 304 estimates the color of the subject based on the calculated differential value (step S109) and then displays the estimated value as a measurement result on the touchscreen 101 (display).

FIG. 9 is a flowchart illustrating details of the image capturing process (step S103) illustrated in FIG. 6. First, the control unit 301 captures one frame of image data and reads the image data from the frame memory 213 (step S201). The control unit 301 may trim the read image data into a predetermined size (for example, 640 by 480 pixels). Next, the control unit 301 performs Fourier transformation on the image data and extracts energy of a high frequency component (step S202).

Next, the control unit 301 calculates an amount of change in the energy of a high frequency component with respect to the immediately previous captured frame (step S203). For example, the control unit 301 calculates a difference ($E(n)-E(n-1)$) between energy $E(n)$ for the immediately previous frame (n) and energy $E(n-1)$ for the previous frame (n-1). The energy of the high frequency component may be a moving average value for a predetermined number of frames. FIG. 10 illustrates an example of a change in energy of a high frequency component among a plurality of frames.

In FIG. 10, the vertical axis represents the energy E of a high frequency component, and the horizontal axis represent temporally-numbered multiple frames of image data. That is, the frame number "1" is image data of a frame initially captured in image capturing, and sequential image capturing is performed while the image capturing continues. In the example of FIG. 10, the difference of the energy $E$ ($E(n)-E(n-1)$) is a positive value for the frame numbers from "2" to "28" and is a negative value for the frame number "29". That is, this indicates that the peak of the energy of the high frequency component is located at the frame number "28".

Next, the control unit 301 compares an amount of change in energy to a predetermined threshold (step S204). The control unit 301 has a threshold of zero, for example, and determines whether or not the difference of energy ($E(n)-E(n-1)$) is greater than or equal to zero (positive or negative). If the amount of change is greater than or equal to zero (positive value) (step S204, NO), the control unit 301 continues image capturing and performs the process of step S201 to step S204 on the next frame. If the amount of change is less than zero (negative value) (step S204, YES), the control unit 301 ends the image capturing process in which the LED 103 emits light, and the process returns to the flowchart of FIG. 7.

According to the image analysis device 100 of the present embodiment, the first image captured with light emission of the LED 103 and the second image captured without light emission of the LED 103 are acquired, and the color of the measurement region is estimated from a differential value of color information of predetermined measurement regions in these images. That is, it is possible to cancel the influence of an external light (environment light) by calculating the differential value and thereby accurately estimate the color of the measurement region based on a known nature (light emission intensity or the like) of an illumination light and the differential value of color information calculated from two types of captured images. As a result, even a user having no device dedicated for skin measurement can perform accurate skin measurement by using a camera of a smartphone or the like without using color samples.

Second Embodiment

An image analysis device 400 according to the second embodiment will be described below. Note that a reference numeral common to the reference numeral provided in the drawings of the first embodiment indicates the same object. Thus, the description of parts common to the first embodiment will be omitted, and different parts will be described in detail.

FIG. 11 is a functional block diagram of the image analysis device 400. In the image analysis device 400, in response to sensing the orientation (inclination) of the image analysis device 400 (the image capturing unit 102) relative to a subject, a gyroscope 218 that is a sensor unit outputs the sensing signal to the control unit 301. The control unit 301 stores angle information corresponding to the sensing signal in the storage 217. The first angle information indicates the orientation (inclination) of the image analysis device 400 at the time when the user instructs start of image capturing. On the other hand, the second angle information indicates the orientation (inclination) of the image analysis device 400 at the time when the focusing distance is reached and thus the first image and the second image are captured.

The measurement region determination unit 303 corrects the setting position of the measurement region while maintaining the positional relationship of the reflection region and the measurement region based on the positional relationship of the image capturing unit 102 and the LED 103 (light emitting unit) and the amount of change in inclination (amount of change in angle). The measurement region determination unit 303 moves the measurement region to maintain the way of irradiation with the illumination light from the LED 103 to be constant.

When the subject is located in the axis direction of the yawing axis of the gyroscope 218, the measurement region determination unit 303 calculates an amount of change in inclination based on rotation angles about the roll axis and the pitch axis of the gyroscope 218. The relationship of an amount of change in the calculated inclination and a corrected position of the measurement region is preferably predefined in the storage 217 or the like.

FIG. 12A and FIG. 12B are diagrams illustrating correction of the measurement region in accordance with an attitude state of the image analysis device 400. In FIG. 12A, the X-axis is the pitch axis, the Y-axis is the roll axis, and the Z-axis is the yawing axis. Directions X1 and X2 indicate rotation directions around the X-axis, and directions Y1 and Y2 indicate rotation directions around the Y-axis. Note that, when there is a rotation around the Z-axis, since no change occurs in the relative relation between the measurement region and the reflection region, the measurement region is not to be corrected. FIG. 12B illustrates which directions in a captured region P the reflection region S and the measurement region M of an illumination light are moved in, respectively, when rotations occur around the X-axis and the Y-axis illustrated in FIG. 12A, respectively.

FIG. 13 is a flowchart illustrating an example of the process performed in the image analysis device 400. An example in which the user uses the measuring application 300 to measure the color (skin color) of the subject (cheek) will now be described.

In the image analysis device 400, once the user starts up the measuring application 300, the control unit 301 disables the AF function of the image capturing unit 102 (step S301). That is, the control unit 301 sets the optical system 201 in a state of a fixed focus. The focusing distance may be defined here so that the size of the captured image becomes optimal in image analysis. For example, the focusing distance may range from 50 mm to 100 mm, or may be the shortest distance that can be set in the image capturing unit 102. The control unit 301 sets a light amount, a color temperature, or a chroma of the LED 103 so that a light environment suitable for image capturing can be obtained and then turns on the LED 103.

Next, in an initial state where the image analysis device 400 is in contact with the cheek (subject) of the user, for example, the control unit 301 starts capturing a subject by using the image capturing unit 102 while causing the LED 103 to emit light (step S302).

Next, the control unit 301 stores first angle information at the time of start of image capturing (step S303). Specifically, when the user taps the touchscreen 101 while causing the image analysis device 400 to be in contact with the cheek, the inclination states in the X-axis direction and the Y-axis direction of the image analysis device 400 are stored as the first angle information.

Subsequently, the control unit 301 continues the image capturing by using the image capturing unit 102 until the focusing distance from the subject (cheek) is reached (step S304). After tapping the touchscreen 101, the user moves the image capturing unit 102 gradually in the vertical direction away from the subject (cheek). Based on change in the sharpness of the image, the control unit 301 determines whether or not the position of the image capturing unit 102 has moved by the focusing distance from the subject (cheek). The image capturing process (step S304) is the same as that of FIG. 9 described above.

Next, the image acquisition unit 302 acquires the captured image (first image) of the subject in the focusing distance (step S305). Specifically, the image acquisition unit 302 acquires image data having the largest energy of a high frequency component out of multiple frames of image data obtained by image capturing. The acquisition process of image data (step S305) may be performed at the same time as the image capturing process described above (step S304).

Next, the control unit 301 captures the subject by using the image capturing unit 102 while stopping light emission of the LED 103 (step S306). In response, the image acquisition unit 302 acquires the captured image (second image) at the focusing distance in a state without light emission, and the control unit 301 acquires second angle information at the focusing distance (step S307).

Next, the measurement region determination unit 303 corrects the setting position of the measurement region by using the first angle information and the second angle information (step S308).

Next, the skin color estimation unit 304 acquires color information in the measurement region of the first image and the second image (step S309). As described above, the measurement region is spaced apart by a predetermined distance away from the reflection region corresponding to the position where the light from the LED 103 regularly reflects (mirror-reflects) at the subject among the first image and the second image. The process of step S308 and step S309 may be performed at the same time.

Next, the skin color estimation unit 304 calculates a differential value of color information in the common measurement region between the first image and the second image (step S310). Then, the skin color estimation unit 304 estimates the color of the subject based on the calculated differential value (step S311) and then displays the estimated value as a measurement result on the touchscreen 101 (display)

FIG. 14 is a flowchart illustrating details of the correction process of the measurement region (step S308) illustrated in FIG. 13.

First, the skin color estimation unit 304 acquires the first angle information and the second angle information stored in the storage 217 (step S401) and then calculates an amount of change in the angle around the X-axis (step S402).

Next, the skin color estimation unit 304 determines whether or not the amount of change in the angle around the X-axis is less than or equal to a threshold (step S403). The threshold for the amount of change in the angle around the X-axis is 6 degrees, for example. If the skin color estimation unit 304 determines that the amount of change in the angle is less than or equal to the threshold (step S403, YES), the process transfers to step S404. On the other hand, if the skin color estimation unit 304 determines that the amount of change in the angle exceeds the threshold (step S403, NO), the process transfers to step S407.

Next, the skin color estimation unit 304 calculates an amount of change in the angle around the Y-axis (step S404) and then determines whether or not the amount of change in the angle around the Y-axis is less than or equal to a threshold (step S405). The threshold for the amount of change in the angle around the Y-axis is 6 degrees, for example. If the skin color estimation unit 304 determines that the amount of change in the angle is less than or equal to the threshold (step S405, YES), the process transfers to step S406. On the other hand, if the skin color estimation unit 304 determines that the amount of change in the angle exceeds the threshold (step S405, NO), the process transfers to step S407.

Next, the skin color estimation unit 304 corrects the setting position of the measurement region so as to maintain the positional relationship of the region where the illumination light from the LED 103 regularly reflects and the measurement region (step S406), and the process returns to the flowchart of FIG. 13 (step S309).

The skin color estimation unit 304 then outputs a message prompting re-measurement through display on the touchscreen 101 or voice (step S407) and terminates the process without going back to the flowchart of FIG. 13. That is, when the image analysis device 400 is inclined from the start of measurement over a range where the measurement region can be corrected, this means that the irradiation condition of the LED 103 has significantly changed, and thus in remeasurement is prompted.

According to the image analysis device 400 of the present embodiment, it is possible to correct the position of the measurement region while maintaining the positional relationship of the reflection region and the measurement region of an illumination light based on the angle information sensed by the gyroscope 218. Therefore, even when the inclination (attitude state) of the image analysis device 400 changes from the time of starting measurement to the time of ending measurement, it is possible to accurately measure the color of the measurement region by maintaining the way of irradiation with an illumination light on the measurement region to a constant level.

Modified Embodiment

The embodiments described above are intended to merely illustrate an example of embodiment in implementing the present invention, and the technical scope of the present invention is not to be construed in a limiting sense by these embodiments. That is, the present invention is not limited to the embodiments described above and can be modified and implemented within a scope not departing from the spirit of the present invention.

In the embodiments described above, while provided only on the backside of the image analysis device 100, the LED 103, which is a light emitting unit, may be provided also on the front side. FIG. 15 is a diagram illustrating a state in the image capturing process of the image analysis device 500. Further, FIG. 16 is a front view illustrating an example of the operating window displayed on an image analysis device 500. This example illustrates that, separately from the image capturing unit 102 and the LED 103 on the backside, an image capturing unit 104 (in-camera) and an LED 105 are provided on the same surface as the display 211 (the touchscreen 101) displaying the operating window (on the front surface of the image analysis device 500), respectively. In this case, since the user can input start and finish instructions of skin color measurement while referring to the operating window displayed on the display 211, there is an advantage of further improved operability.

Further, while the case where the LED 103 is the light emitting unit has been described in the above embodiments, the light emitting unit is not limited to the LED 103 only. For example, the display itself of the touchscreen 101 can be configured to also serve as a light emitting unit. In this case, in the same manner as FIG. 15 described above, there are advantages that skin color measurement using an in-camera is enabled and irradiation range can be precisely set compared to the case of using the LED 103.

While the case that each of the image analysis devices 100, 400, and 500 measures the color of the user's cheek has been described in the above embodiments, the measuring part is not limited to the user's cheek. The image analysis devices 100, 400, and 500 can be applied to measure various parts of the human body surface such as skin, a scalp, a nail, a hair, a lip, or the like. Similarly, a part measured by the image analysis devices 100, 400, and 500 is not limited to a human body. The image analysis device 100, 400, and 500 can be applied to measure the color of any object other than a human body.

While the method of measuring (estimating) the color of a subject based on the first image and the second image captured when each of the image analysis devices 100, 400, and 500 reaches a focusing distance from a subject has been described in each of the above embodiments, the measuring method is not limited thereto. For example, in the case of a mobile phone having a 3D scanning function, it is possible to use captured images (the first image and the second image) at a position other than focusing distance to measure the color of the subject in the same manner as the case of each embodiment by performing correction of the distance on the illumination condition based on Bidirectional Reflectance Distribution Function (BRDF) from the distance at image capturing.

Reference Signs List

100,400,500 image analysis device
101 touchscreen (display)
102,104 image capturing unit
103,105 LED (light emitting unit)
213 frame memory
214 CPU
215 RAM
217 storage
218 gyroscope
301 control unit
302 image acquisition unit
303 measurement region determination unit (determination unit)
304 skin color estimation unit (estimation unit)

The invention claimed is:

1. An image analysis device comprising:
   an image capturing unit that captures a subject;
   a light emitting unit that emits light to the subject;
   a sensor unit that senses an inclination of the image capturing unit relative to the subject;
   a control unit that causes the image capturing unit to capture an image of the subject while controlling light emission of the light emitting unit; and
   a determination unit that, based on a positional relationship of the image capturing unit and the light emitting unit and the inclination, determines a measurement region spaced apart by a predetermined distance from a reflection region corresponding to a position in the image where a light from the light emitting unit regularly reflects at the subject.

2. The image analysis device according to claim 1 further comprising an estimation unit that estimates color of the subject based on color information on a reference pixel included in the measurement region of the image,
   wherein, based on a positional relationship of the image capturing unit and the light emitting unit and an amount of change in the inclination, the determination unit corrects a position of the measurement region while maintaining a positional relationship of the reflection region and the measurement region.

3. The image analysis device according to claim 2,
   wherein the sensor unit is a gyroscope, and
   wherein, when the subject is located in an axial direction of a yawing axis of the gyroscope, the determination unit calculates the amount of change in the inclination based on rotation angles about a roll axis and a pitch axis of the gyroscope.

4. The image analysis device according to claim 2,
   wherein the image includes the color information of an RGB color specification system, and wherein the estimation unit estimates the color based on the color information of an XYZ color specification system converted from the RGB color specification system.

5. The image analysis device according to claim 2, wherein the control unit causes the image capturing unit to capture the image while disabling a white balance function.

6. The image analysis device according to claim 1, wherein both the image capturing unit and the light emitting unit are provided on a surface opposite to a display that displays an operating window.

7. The image analysis device according to claim 1, wherein both the image capturing unit and the light emitting unit are provided on the same surface as a display that displays an operating window.

8. The image analysis device according to claim 7, wherein the display also serves as the light emitting unit.

9. The image analysis device according to claim 1, wherein the subject is a human body surface.

10. An image analysis method comprising steps of:
    causing an image capturing device to capture an image of a subject while controlling light emission of a light emitting device to the subject;
    sensing an inclination of the image capturing device relative to the subject by using a sensor; and
    based on a positional relationship of the image capturing device and the light emitting device and the inclination, determining a measurement region spaced apart by a predetermined distance from a reflection region corresponding to a position in the image where a light from the light emitting device regularly reflects at the subject.

11. A non-transitory storage medium in which a program is stored, the program causing a computer to perform steps of:
    causing an image capturing device to capture an image of a subject while controlling light emission of a light emitting device to the subject;
    sensing an inclination of the image capturing device relative to the subject by using a sensor; and
    based on a positional relationship of the image capturing device and the light emitting device and the inclination, determining a measurement region spaced apart by a predetermined distance from a reflection region corresponding to a position in the image where a light from the light emitting device regularly reflects at the subject.

* * * * *